United States Patent [19]

Lin et al.

[11] Patent Number: 5,276,244
[45] Date of Patent: Jan. 4, 1994

[54] SEPARATION OF ALUMINUM ALKYLS FROM OLEFINS USING MODIFIED INORGANIC MEMBRANES

[75] Inventors: Kaung-Far Lin; William B. Waites, both of Baton Rouge, La.

[73] Assignee: Ethyl Corporation, Richmond, Va.

[21] Appl. No.: 39,663

[22] Filed: Mar. 30, 1993

[51] Int. Cl.$^5$ .................. C07C 7/144; B01D 11/00
[52] U.S. Cl. .................. 585/818; 210/644; 210/651
[58] Field of Search .............. 585/818; 210/644, 651

[56] References Cited

U.S. PATENT DOCUMENTS

| | | | |
|---|---|---|---|
| 3,149,179 | 9/1964 | Bowden | 260/683.15 |
| 3,617,553 | 11/1971 | Westaway et al. | 210/23 |
| 3,637,885 | 1/1972 | McClaflin | 260/677 A |
| 3,645,891 | 2/1972 | Goldup et al. | 210/23 |
| 4,411,790 | 10/1983 | Arod et al. | 585/818 |
| 5,151,182 | 9/1992 | Perry et al. | 210/500 |

OTHER PUBLICATIONS

Product Information "Membralox® Ceramic Membrane Filtration Products" U.S. Filter Corporation, 1982, pp. 1-4.
Product Information "Membralox® Ceramic Membrane Separation Systems", Alcoa Separations Technology Division, pp. 1-8 (date unavailable).

*Primary Examiner*—Anthony McFarlane
*Assistant Examiner*—Nhat D. Phan
*Attorney, Agent, or Firm*—David M. Bunnell

[57] ABSTRACT

A process for separating a mixture of aluminum alkyl and alpha-olefin, said process comprising contacting a silica modified inorganic membrane filter with said mixture and recovering, as the permeate, an alpha-olefin fraction which contains a lower concentration of aluminum alkyl than in said mixture, as the retentate, an aluminum alkyl fraction which contains a higher concentration of aluminum alkyl than in said mixture.

20 Claims, No Drawings

SEPARATION OF ALUMINUM ALKYLS FROM OLEFINS USING MODIFIED INORGANIC MEMBRANES

BACKGROUND OF THE INVENTION

The invention relates generally to membrane separation processes and more specifically to a process for separating aluminum alkyls, such as trialkylaluminums, from olefins using pore size modified inorganic membranes.

Aluminum alkyls and especially triethylaluminum are used in the so-called Ziegler chain growth process to prepare linear alpha-olefins. The process involves the reaction of triethylaluminum (TEA) and ethylene at temperatures in the range of 200°-500° F. and pressures in the range of 2000 to 5000 psig to yield a mixture of tri-$C_2$-$C_{20+}$ alkylaluminum compounds and $C_2$-$C_{20}$ olefins. Linear alpha-olefins are then recovered from the alkylaluminum compounds by olefin displacement using ethylene, 1-butene or mixtures thereof as the displacing olefin. To the extent possible, the aluminum alkyls are separated from the olefins and recycled to the chain growth reactor. One limiting factor in the amount of aluminum alkyls that can be recovered is that when the boiling points of the aluminum alkyls and the olefins are similar, and/or when heat causes decomposition, separation by distillation is difficult. The aluminum alkyls can be removed by oxidation and hydrolysis to generate alcohols, but this causes a loss of the expensive aluminum alkyl materials and the alcohols are generally of little or no commercial value.

U.S. Pat. No. 3,149,179 discloses the use of membrane permeation to separate TEA from linear olefins. Preferred membranes are those selected from synthetically derived plastics which are predominantly hydrocarbon in nature and especially polyethylene. Polyesters are also mentioned. No working example is provided and the process is described in mostly general terms. In fact, we have found that a successful membrane separation of aluminum alkyls and alpha-olefins is difficult to achieve even considering the advances in membrane technology which have occurred in the approximately 30 years since the issuance of the U.S. Pat. No. 3,149,179. In our copending application Ser. No. 08/008,951, filed Jan. 26, 1993, a process is described which successfully separates aluminum alkyls from alpha-olefins by using a polyphenylene oxide-derived membrane at elevated pressures.

SUMMARY OF THE INVENTION

We have now found that certain pore size modified inorganic membranes can also be used to separate aluminum alkyls from alpha-olefins and, especially, heavy aluminum alkyls and alpha-olefins having carbon numbers of $C_{14}$ to $C_{28}$.

In accordance with this invention there is provided a process for separating a mixture of aluminum alkyl and alpha-olefin, said process comprising contacting a silica modified inorganic membrane filter with said mixture so as to obtain, as the permeate, an alpha-olefin fraction which contains a lower concentration of aluminum alkyl than in said mixture and, as the retentate, an aluminum alkyl fraction which contains a higher concentration of aluminum alkyl than in said mixture.

DESCRIPTION OF THE PREFERRED EMBODIMENTS

The filter structure can have any conventional configuration such as a flat disk or a tube. The basic membrane filters, can, for example, comprise a macroporous support block of sintered ceramic, metal (such as stainless steel), glass or carbon having one or more parallel longitudinal channels at whose surface is formed a porous membrane layer. The block can be formed, for example, by sintering multiple layers of alumina or zirconia to form a monolithic structure. Such membrane filters are commercially available in pore sizes ranging from about 50 to 1000 Å. Pore size is determined by the procedure described by D. E. Fain, "A Dynamic Flow—Weighted Pore Size Distribution Test" presented at The First International Conference on Inorganic Membranes, Montpellier France in July 1989. The filters are modified to reduce their average pore size by depositing silica on the membrane filter by chemical vapor deposition. This process is known in the art. Typically, such silica modified membranes are prepared by introducing tetraethyl orthosilicate in a carrier gas to the filter structure and then decomposing the tetraethyl orthosilicate at a temperature above 300° C. to form a thin film of $SiO_2$ on the pore wall of the filter. Preferably, the silica modified membrane filters for use in aluminum alkyl separation have average pore sizes in the range of from about 10 to 500 Å and more preferably in the range of from about 20 to 100 Å. For example, ceramic membranes having an original average pore size of about 50 Å are coated with 1 to 1.5 $\mu M$ layers of $SiO_2$ to provide silica modified membrane filters having average pore sizes of from about 3 to 40 Å.

The separation process can be conducted in either a batch or continuous mode. The aluminum alkyl/olefin feed can be continuously delivered into one end of the channel or channels in the filter block and then discharged (retentate) from the other end and, optionally, recycled. The olefin filtrate (permeate) passes through the membrane layer and is collected in configuration can be reversed with the permeate being collected in the channels. Other alternatives for filter configuration and delivery schemes can be used. For example, the channel can be formed as a tube bundle such as in a shell and tube type heat exchanger or a honeycomb configuration.

The aluminum alkyl separation process is preferably operated at temperatures from about 0° to 200° C., with higher temperatures providing increased flux. The process can be operated at pressures ranging from atmospheric to about 4000 psig or above and preferably at pressures of from about 200 psig to 2000 psig.

The process can be employed to separate mixtures containing from about 0.1 up to about 80 wt. %, based on the weight of the total mixture, of aluminum alkyl, and especially mixtures of trialkylaluminum compounds, wherein each alkyl group contains from about 2 to 30 carbon atoms, and liquid, linear alpha-olefins having from about 2 to 30 carbon atoms. It is especially suitable for separating mixtures which contain from about 0.5 to 30 wt. % of total mixture of heavy ($C_{14}$ and above) trialkylaluminum compounds combined with heavy ($C_{14}$ and above) alpha-olefins. Typical examples are mixtures of predominantly $C_{14}$ to $C_{28}$ alpha-olefins containing from about 3.0 to 30 wt. % of $C_{14}$ to $C_{24}$ trialkylaluminum compounds (about 0.15 to 1.5 wt % aluminum). Such mixtures may also contain small amounts of up to about 10 wt. % of lighter, ($C_6$ to $C_{12}$) material. The process has the advantage of producing a permeate alpha-olefin stream which is substantially free of aluminum alkyls (less than 0.1 wt. % aluminum) and a retentate stream which is more concentrated in aluminum alkyl by a factor of at least about 1.1 or more and, preferably of at least about 1.5.

The process is further illustrated by, but is not intended to be limited to, the following examples.

EXAMPLE 1

A bottoms stream from an ethylene chain growth process was fed through a silica modified alumina membrane filter module and provided an olefin permeate which was free of aluminum alkyl. The bottoms stream contained a mixture of about 20 wt. % $C_6$ to $C_{24}$ aluminum alkyl (85 wt. % of which were $C_{14+}$) and about 80 wt. % of $C_6$ to $C_{28}$ hydrocarbons (97.5 wt. % of which were $C_{14+}$ olefins). Small amounts of vinylidene, internal olefins and paraffin were also present in the mixture. The initial aluminum concentration in the feed was about 0.73 wt. % aluminum. The membrane filter was a single tube filter of gamma alumina (original pore size 50 Å) which had been subjected to chemical vapor deposition to deposit silica on the filter so as to reduce the average pore size to 32.8 Å. The inner diameter of the filter tube was about 7 mm, the length was length was 22.5 cm and the surface area of the filter element was 0.00557 $M^2$. The modified filter had the following solvent permeabilities.

| Hexane: | 35° C. | 0.1075 | $L/M^2/hr/atm$ |
|---|---|---|---|
| | 27° C. | 0.0948 | $L/M^2/hr/atm$ |
| Hexadecane: | 179° C. | 0.361 | $L/M^2/hr/atm$ |
| | 140° C. | 0.276 | $L/M^2/hr/atm$ |
| | 100° C. | 0.189 | $L/M^2/hr/atm$ |
| | 60° C. | 0.095 | $L/M^2/hr/atm$ |

The sample stream was pumped through a preheater to the inlet of the membrane filter module at a flow rate of 20 cc/min. The temperature of the sample passing through the module was 100° C. and the pressure was 200 psig. The stream was recycled to the feed stream ahead of the preheater. The olefin permeate which passed through the filter element into the outer portion was collected in a container and analyzed for aluminum. No aluminum was detected in the permeate (less than 0.002 wt. % aluminum).

What is claimed is:

1. A process for separating a mixture of aluminum alkyl and alpha-olefin, said process comprising contacting a silica modified inorganic membrane filter with said mixture so as to obtain, as the permeate, an alpha-olefin fraction which contains a lower concentration of aluminum alkyl than in said mixture and, as the retentate, an aluminum alkyl fraction which contains a higher concentration of aluminum alkyl than in said mixture.

2. The process of claim 1 wherein said process is at a pressure of from about atmospheric to 4000 psig and a temperature of from about 0° to 200° C.

3. The process of claim 2 wherein said process is at a pressure of from about 200 psig to 2000 psig.

4. The process of claim 2 wherein said modified inorganic membrane filter comprises a porous ceramic support originally having a pore size of 50 to 1000 Å on which is coated a layer of silica so as to provide a membrane filter having an average pore size of from about 3 to 500 Å.

5. The process of claim 4 wherein said ceramic support is sintered alumina having an average pore size of about 50 Å on which is coated a 1 to 1.5 µM layer of silica so as to provide a membrane filter having an average pore size of from about 5.5 to 40 Å.

6. The process of claim 1 wherein said mixture contains from about 0.1 to 80 wt. % aluminum alkyl.

7. The process of claim 1 wherein said mixture contains from about 0.5 to 30 wt. % aluminum alkyl.

8. The process of claim 1 wherein said alpha-olefin contains from about 2 to 30 carbon atoms.

9. The process of claim 1 wherein said alpha-olefin comprises a $C_2$ to $C_{30}$ linear alpha-olefin.

10. The process of claim 1 wherein said alpha-olefin comprises a mixture of $C_{14}$ to $C_{28}$ linear alpha-olefins.

11. The process of claim 1 wherein said alpha-olefin is a mixture of two or more $C_{14}$ to $C_{28}$ linear alpha-olefins.

12. The process of claim 1 wherein said filter comprises a block of sintered ceramic having one or more longitudinal parallel passageways through which said mixture is feed, said block being mounted in an outer shell which is adapted to receive the alpha-olefin permeate which passes through said filter.

13. The process of claim 12 wherein said sintered ceramic is selected from alumina and zirconia.

14. The process of claim 13 wherein said alumina is gamma alumina.

15. The process of claim 4 wherein said membrane filter has an average pore size of from about 20 to 100 Å.

16. The process of claim 1 wherein said permeate is substantially free of aluminum alkyl.

17. The process of claim 5 wherein said permeate is substantially free of aluminum alkyl.

18. The process of claim 1 wherein the concentration of aluminum alkyl in the retentate is increased by a factor of at least about 1.1.

19. The process of claim 5 wherein the concentration of aluminum alkyl in the retentate is increased by a factor of at least about 1.5.

20. The process of claim 19 wherein said permeate contains less than about 0.1 wt. % aluminum.

* * * * *